United States Patent
Holschneider et al.

(10) Patent No.: US 6,554,822 B1
(45) Date of Patent: Apr. 29, 2003

(54) MICROBOLUS INFUSION PUMP

(75) Inventors: Daniel P. Holschneider, Los Angeles, CA (US); Oscar U. Scremin, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/561,394

(22) Filed: Apr. 28, 2000

Related U.S. Application Data (60) Provisional application No. 60/167,104, filed on Nov. 23, 1999, and provisional application No. 60/131,975, filed on Apr. 30, 1999.

(51) Int. Cl.⁷ .............................................. A61K 9/22
(52) U.S. Cl. ................. 604/892.1; 604/30; 604/156; 604/212
(58) Field of Search ................. 604/890.1, 891.1, 604/892.1, 27, 30, 31, 33, 65, 67, 246, 247, 248, 212–216, 153, 156, 19, 20; 600/9, 12, 29, 30

(56) References Cited

U.S. PATENT DOCUMENTS

| | | | |
|---|---|---|---|
| 3,951,147 A | 4/1976 | Tucker et al. | 128/260 |
| 4,350,155 A | 9/1982 | Thompson | 128/213 |
| 4,619,653 A | 10/1986 | Fishell | 604/891 |
| 4,673,391 A | 6/1987 | Kondo et al. | 604/141 |
| 4,772,263 A | 9/1988 | Dorman et al. | 604/132 |
| 5,785,688 A | 7/1998 | Joshi et al. | 604/141 |
| 5,836,935 A | 11/1998 | Ashton et al. | 604/891.1 |
| 6,048,328 A | 4/2000 | Haller et al. | 604/93 |
| 6,206,914 B1 * | 3/2001 | Soykan et al. | 623/1.42 |
| 6,409,698 B1 * | 6/2002 | Robinson et al. | 604/19 |

FOREIGN PATENT DOCUMENTS

| | | | |
|---|---|---|---|
| DE | 293 055 A5 | 10/1983 | A61M/5/142 |
| WO | WO 97/27829 | 8/1997 | |

OTHER PUBLICATIONS

Buchwald, H.; Rohde, T., *International Study Group for Implantable Infusion Devices 1996; The World's Only Implantable Infusion Pump Study*, ASAIO Journal 132–136 (1997).

Buchwald, H.; Rohde, T., *Implantable Pumps; Recent Progress and Anticipated Future Advances*, ASAIO Journal 772–778 (1992).

Wigness, D.B., et al., *The Spring–driven Implantable Pump; A Low–cost Alternative*, ASAIO Journal M454–M457 (1992).

* cited by examiner

*Primary Examiner*—Gregory Huson
*Assistant Examiner*—Peter deVore
(74) *Attorney, Agent, or Firm*—Bingham McCutchen LLP

(57) ABSTRACT

An implantable microbolus infusion pump is disclosed which includes an elastically deformable reservoir, an electrically activated microvalve, and a remotely activated control system. The control system includes a sensor that can be remotely activate, for example, magnetically or by infrared light. The pump can provide bolus infusion of pharmacologic agents. The pump is also capable of providing sequential release of a plurality of drugs.

25 Claims, 5 Drawing Sheets

MICROBOLUS INFUSION PUMP

RELATED APPLICATION DATA

This application claims priority to provisional applications Serial No. 60/131,975, filed Apr. 30, 1999, and Ser. No. 60/167,104, filed Nov. 23, 1999, the entire disclosures of which are incorporated herein by reference in their entirety.

FIELD OF THE INVENTION

The invention relates to an implantable pump for drug infusion and more particularly to a pump having a remotely activatable valve for triggering drug release.

BACKGROUND

Implantable infusion pumps allow the directed delivery of pharmacological agents to discrete locations within an animal either as a discrete dose or as a constant infusion.

Currently available technology does not permit acute bolus infusion of pharmacologic agents in conscious, behaving, non-tethered, small animals. This is a handicap for the fields of pharmacology, animal behavior, physiology, and imaging in that rats and mice are the most widely used and cost-effective animal models. Small, implantable slow-release osmotic pumps are commercially available and are widely used by researchers across numerous disciplines. Slow-release pumps, however, allow only examination of chronic drug effects. Acute bolus injection only is possible in restrained, immobilized or tethered animals. For many applications, however, the physical aspects of immobilization or the stress of needle sticks themselves changes the animal's behavior, physiology or pharmacologic response, leaving the physiologic significance of any results up to interpretation.

It is well known that the presence or absence of stress may substantially change an animal's behavior. Even minor routine handling procedures can induce a marked stress in animals, although the animal has been trained to this procedure and looks quiet. Handling an animal or drug injection by needle will largely suppress behaviors such as aggression, sleep, and mating at the time of occurrence. This has made it difficult to study the neurochemical basis of behaviors which otherwise might be characterized using acute administration of pharmacologic agents. Examination of the acute pharmacologic effects on a behavior at the time of its occurrence has been tried in tethered animals connected via a head cap or body port to an external catheter that is supported by a swivel joint and balance arm. Such techniques are practical only in the study of behaviors of animals in isolation and are limited to a subset of behaviors which present a low risk of entanglement of the animal with its cable. The extent to which the stress of tethering reshapes 'normal' behavior in these paradigms is likely substantial.

In the field of neurobehavioral pharmacology, there is a critical need for a means of acutely administering pharmacologic agents in a nonstressful manner.

Although implantable infusion pumps are known, none meet this need. For example, a compact spring-activated pump has been disclosed (Wigness, B. D., Dorman, F. D., Rohde, T. D. and Buchwald, H. The spring-driven implantable pump. A low-cost alternative, *Asaio Journal*, 38 (1992) M454–457; Dorman and Buchwald, U.S. Pat. No. 4,772, 263). This pump does not address the need for a remotely-activated infusion pump capable of bolus infusions. Likewise, Ashton et al. (U.S. Pat. No. 5,836,935) disclose an implantable infusion pump for the controlled release of a drug, but does not recognize the need for remote activation or a control valve.

There exists a need for an implantable infusion pump capable of infusing a bolus of drug that can be remotely operated, is compact and can be readily manufactured.

SUMMARY

The invention provides a pump for drug delivery having a reservoir with an elastically deformable member, wherein the reservoir is in fluid communication with an outlet catheter, having an electrically activated valve in fluid communication with the reservoir, and having a control system containing a sensor such that the valve can be remotely operated. The sensor can be sensitive to a magnetic field or any electromagnetic radiation including, for example, infrared light. In one embodiment, the pump is compact and can be manufactured at a low cost.

In a preferred embodiment, the valve is closed in its resting state such that upon activation of the control system, the pump can provide a bolus injection of an infusate. In a preferred embodiment, the valve is a solenoid valve.

The entire pump can be implanted in an organism subcutaneously or a portion of the pump can be mounted percutaneously. In one embodiment, the entire pump can be implanted in an animal. In another embodiment, the reservoir and drug delivery channel can be implanted subcutaneously, while the sensor is attached percutaneously.

The pump can be of such a size that it can be implanted into a small mammal, for example a rodent. In various embodiments, the pump has a reservoir with a volume of between about 0.1 milliliters (ml) and about 10 ml, preferably between about 0.1 ml and about 5 ml, and even more preferably between about 0.1 ml and about 2 ml.

In one embodiment, the elastically deformable member of the reservoir acts as a septum and can reseal after puncture by a hypodermic needle. The reservoir also can contain an refilling injection port. In one embodiment, the refilling injection port is a septum that reseals after puncture by a hypodermic needle. The refilling injection port also can be tubing in fluid communication with the reservoir with a septum that reseals after puncture by a hypodermic needle.

The pump also can contain an ejection chamber in fluid communication with the valve and the outlet catheter. In one embodiment, the ejection chamber is a coil of tubing.

DETAILED DESCRIPTION

The invention provides a pump for drug delivery having a reservoir with an elastically deformable member, wherein the reservoir is in fluid communication with an electrically activated valve, an outlet catheter in fluid communication with the reservoir, and having a control system containing a sensor such that the valve can be remotely operated. The sensor can be sensitive to a magnetic field or any electromagnetic radiation including, for example, infrared light. In one embodiment, the pump is compact and can be manufactured at a low cost.

The pump can be used in any suitable animal including, for example, humans, apes, monkeys, chimpanzees, pigs, cows, sheep, goats, rabbits, dogs, cats, rats and mice. The compact nature of the design allows for the pump to be manufactured of such a size as to be useful particularly in small animals, such as a rodent including, but not limited to, a rat and a mouse. The pump can be used to deliver any fluid or fluid containing a pharmacologic agent.

The pump particularly is useful for animal studies including the estimation of lethal doses (LD50) and effective doses (ED50) in the absence of stress, which is known to offset these measurements in acute toxicological, pre-clinical evaluation of a drug. In addition, the pump is useful for studying acute drug effects on physiologic function in normal and disease states (e.g. cardiovascular parameters, temperature, brain electrical activity when used in conjunction with telemetry systems). The pump is useful in the estimation of the acute effects of pharmacologic agents (e.g. agonists and antagonists) on animal behaviors requiring minimal intervention (e.g. mating, sleep, circadian rhythms, etc.), and for the neuroimaging of regional brain activation during animal behaviors.

Figure 1:
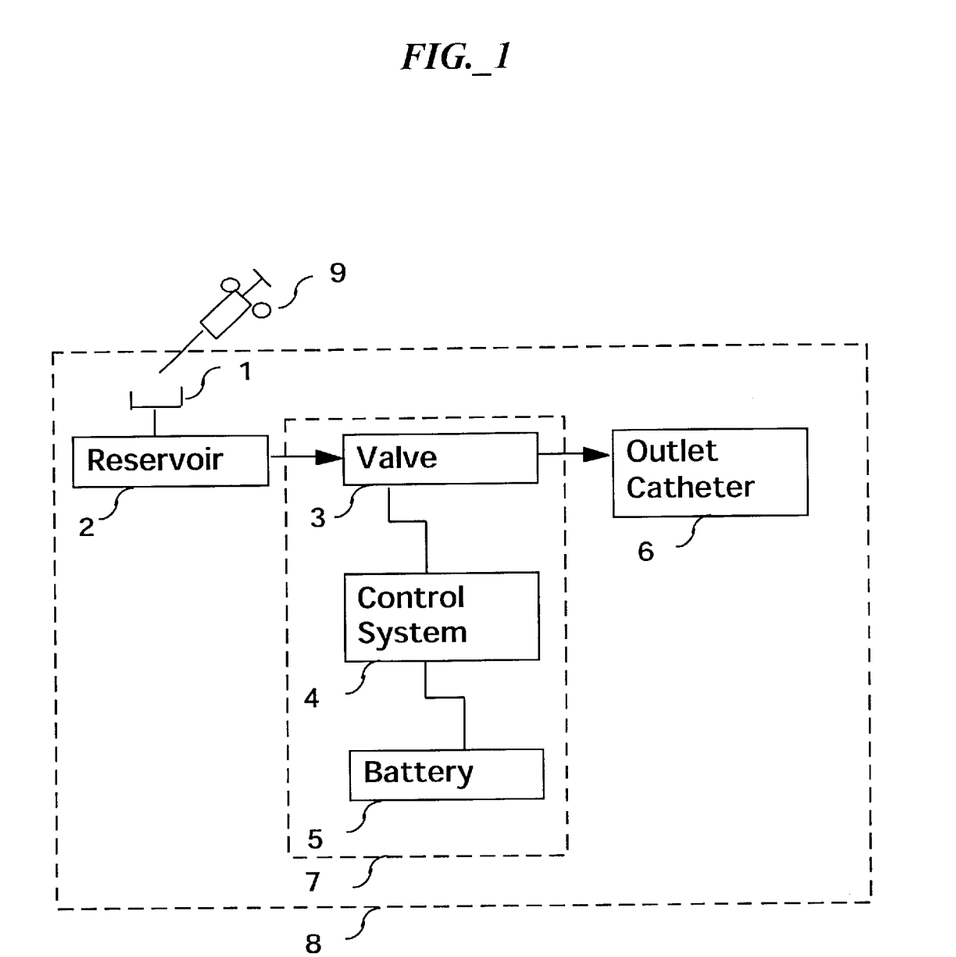
FIG. 1 shows a schematic view of a single chamber pump.

As shown in FIG. 1, one embodiment of the pump has a reservoir 2 in fluid communication with an outlet catheter. The valve 3, control system 4 including battery 5, can be contained in a hermetically sealed module 7. Sealing can be accomplished, for example, by dipping the apparatus in beeswax and coating the apparatus with a biocompatible polymer, for example a silicone. Valve 3 is in fluid communication with reservoir 2 and outlet catheter 6. In the embodiment illustrated in FIG. 1, the reservoir also contains an injection port 1 for refilling the reservoir using a hypodermic syringe 9. The entire device shown in FIG. 1 can be implanted beneath a cutaneous layer 8.

Figure 7:
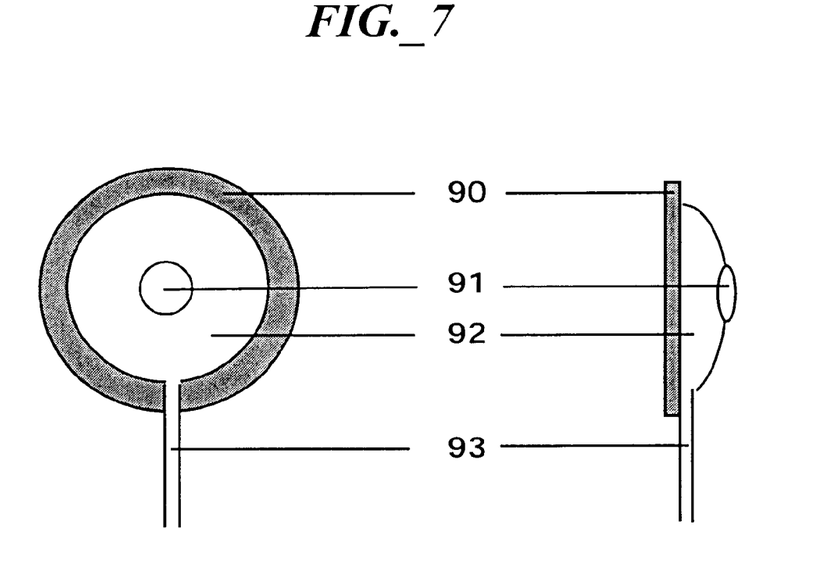
FIG. 7 shows a view of a reservoir unit.

A hollow reservoir 2 suitable for use with the invention is elastically deformable such that it can be filled with an infusate at a positive pressure. The elasticity of the reservoir provides the force to deliver the drug. The reservoir can be constructed from any suitable material or materials including, for example, a polymeric material. In one embodiment, the elastically deformable reservoir member is a silicone disc spring or a Belleville washer. In one embodiment, a reservoir can be constructed from two Belleville washers joined to form an expandable reservoir. As shown in FIG. 7, a reservoir also can be constructed from a substantially rigid backing material 90 and an elastically deformable reservoir member 92 with an integral injection port 91. The reservoir is in fluid communication with tubing 93. In another embodiment, a pump can have multiple reservoirs.

In another embodiment, the reservoir is a piece of elastically deformable tubing, for example silicone tubing, that has been sealed on one end. Such a sealed tubing can be pressurized to form a balloon. The reservoir also can be a balloon made of a semipermeable material (e.g., silastic) filled with a hyperosmotic solution. Such balloons absorb water from the surrounding tissue, and thus maintain themselves in an inflated state in which hydrostatic pressure is equal and opposite to osmotic pressure regardless of volume (assuming that the inflation required to reach this pressure causes a negligible dilution of the original salt concentration). Following a partial emptying of such a reservoir, these balloons self-inflate after a period of hours to days in preparation for a potential second discharge.

A reservoir also can contain other pressurizing devices including, for example, a spring. Other suitable reservoirs include a dual chambered reservoir, wherein one chamber contains the infusate and the other is pressurized with a gas or other propellant. In one embodiment, pressure is generated in this chamber through electrolysis of an electrolytic fluid, as disclosed, for example, by U.S. Pat. Nos. 5,785,688 and 5,681,435.

The entire structure is made of material which is compatible with the animal tissue with which it comes in contact. In one embodiment all components are biocompatible or are coated with a biocompatible material, for example, a medical grade silastic.

In one embodiment, the reservoir is filled with infusate through the outlet catheter while the valve is held in an open position. In another embodiment, the reservoir can contain an inlet port 1. The inlet port 1 allows filling of the reservoir while the valve is closed and also when the device is implanted in an organism. An inlet port can be a septum which can be pierced by a needle for delivery. In another embodiment, the material of all or part of the reservoir acts as an inlet port. In this embodiment, the material of the reservoir acts as a septum and can be punctured by a hypodermic needle and will reseal after puncture. In one embodiment, the septum material is rubber. In another embodiment, the inlet port is a tube containing a resealable septum in fluid communication with the reservoir. Such a tube can be mounted either subcutaneously or percutaneously, to allow easy refilling of the reservoir. Such an inlet port also can contain a membrane filter to prevent debris or infectious agents from entering the reservoir. In such an embodiment, the filter membrane is located between the reservoir and the septum, forming an antechamber.

Figure 2:
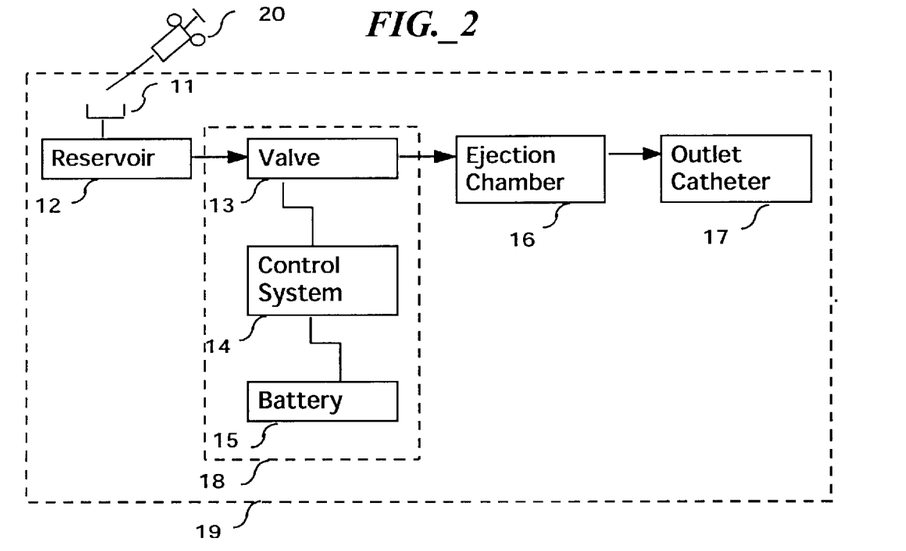
FIG. 2 shows a schematic view of a single reservoir pump with a separate ejection chamber.

As shown in FIG. 2, a pump also can contain a separate ejection chamber 16 in fluid communication with the outlet catheter 17, valve 13, and the reservoir 12. As in FIG. 1, the reservoir can be equipped with an injection port 11. Valve 13 is controlled by control system 14 and powered by battery 15. The ejection chamber 16 can be any suitable material, for example, a polymeric tubing. In a preferred embodiment, the tubing is biocompatible or is coated with a biocompatible material. In various embodiment, the ejection chamber is polyethylene, polytetrafluoroethylene, silastic or polyurethane tubing. It is often convenient to provide an ejection chamber as a coil. In one embodiment, compartmentalization of the coiled ejection chamber containing the pharmacologic agent allows easy excision of this module from the implant after euthanasia of the animal. This is of particular importance for applications involving radioactive compounds. Compartmentalization also allow a cost-effective reutilization of the components of the MIP device in subsequent experiments. The control system and reservoir can be provided as a reusable module to which a separate ejection chamber and outlet catheter can be attached. The pump components also can be separated to allow distribution of the device in small animals such as mice. In one embodiment, the reservoir can be implanted in the peritoneal cavity and connected with tubing to a subcutaneously mounted control system and ejection chamber.

One of skill in the art will recognize that the dimensions and volumes of the reservoir, ejection chambers and outlet catheter should be chosen to be appropriately sized for the animal in which they will be implanted. In one embodiment, a reservoir can have a volume of about 0.1 ml to about 5 ml. In a preferred embodiment, a reservoir has a volume of about 0.1 to about 2 ml. An ejection chamber suitable for use in a mouse, for example, can contain about 150 microliters (ul) in volume while an ejection chamber suitable for use in a rat, for example, can contain about 900 ul.

The dimensions of tubing also can be chosen to vary the overall volume of the device itself. Implantation in smaller animals will require, generally, a smaller overall device. When a smaller device is desired, chambers can be constructed using tubing of wider diameter and shorter length. The consequent reduction in surface area of the tubing should minimize the amount of tubing material.

Likewise, the force of the elastically deformable reservoir member should be tuned to deliver the infusate at a pressure appropriate for the infusion delivery site. For example, higher pressure will be required for example for delivery to the relatively high pressure arterial system of an animal versus that required for venous delivery. An infusion site can be, for example, arterial, venous, subcutaneous, intraperitoneal or intracranial.

A pump of the invention can be constructed to deliver a drug at a defined rate. The rate of delivery will depend on a number of factors including, but not limited to, the pressure of the reservoir compared to the infusion site, the length, material composition and diameter of the ejection chamber and outlet catheter, the presence or absence of a flow restriction device or membrane, and the size and type of valve used. An elastically deformable member can be chosen to maintain a substantially constant delivery pressure by varying the dimensions or material of the elastically deformable material used.

The sequential release of several drugs can be achieved by separating drugs within the tubing of the ejection chamber or outlet catheter air or fluid spacers. A preferred fluid spacer is a saline spacer. Bolus release of each drug will be discrete, provided that the intervening saline spacer is large enough to account for any error related to the timing of infusion.

To achieve complete delivery of a drug contained in ejection chamber 16, the volume of the reservoir should be greater than the combined volume of the ejection chamber 16 and the outlet catheter 17.

A valve useful for the invention can control fluid flow. A valve can have opened and closed states only or can be continuously adjustable to control flow rate. In one embodiment, a valve is a solenoid valve. In a preferred embodiment, a valve is a solenoid valve which is closed in the resting state, minimizing power consumption and preventing inadvertent infusate release.

Figure 3:
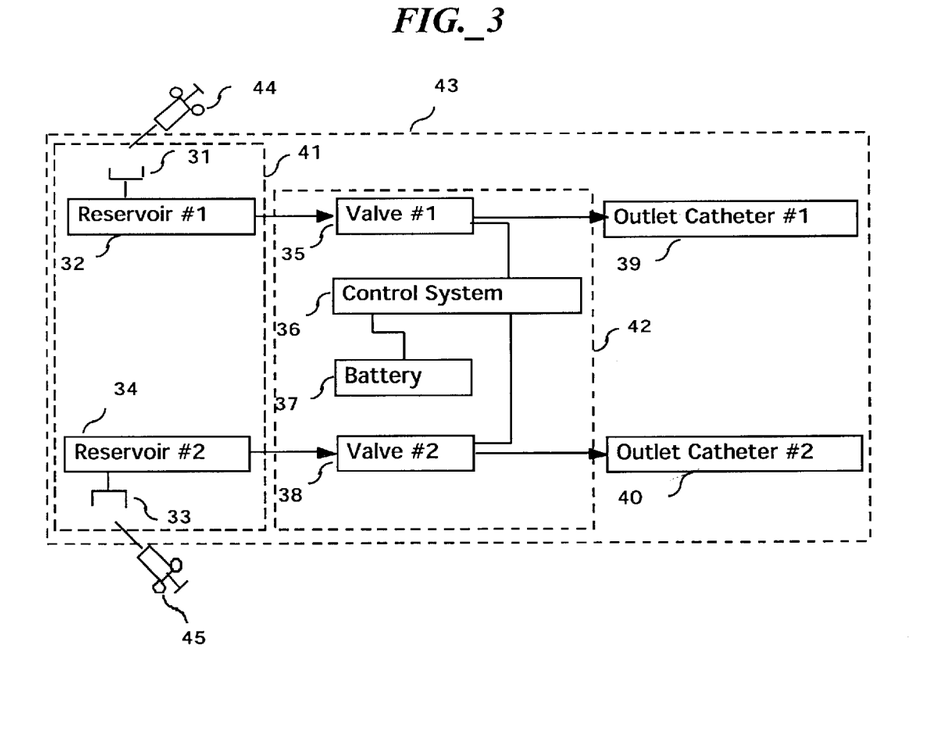
FIG. 3 shows a schematic view of a dual reservoir pump.

A pump of the invention can contain one or more reservoirs controlled by a single or multiple control systems. A pump is shown in FIG. 3 with first and second reservoirs 32 and 34, each with an injection port 31 and 33. Each reservoir is in fluid communication with a valve (35 and 38) which are controlled by control system 36 powered by battery 37. The control system can be designed such that release of infusate from reservoir 32 and reservoir 34 occur simultaneously, or can be controlled independently. The dual reservoirs deliver through outlet catheters 39 and 40.

Figure 4:
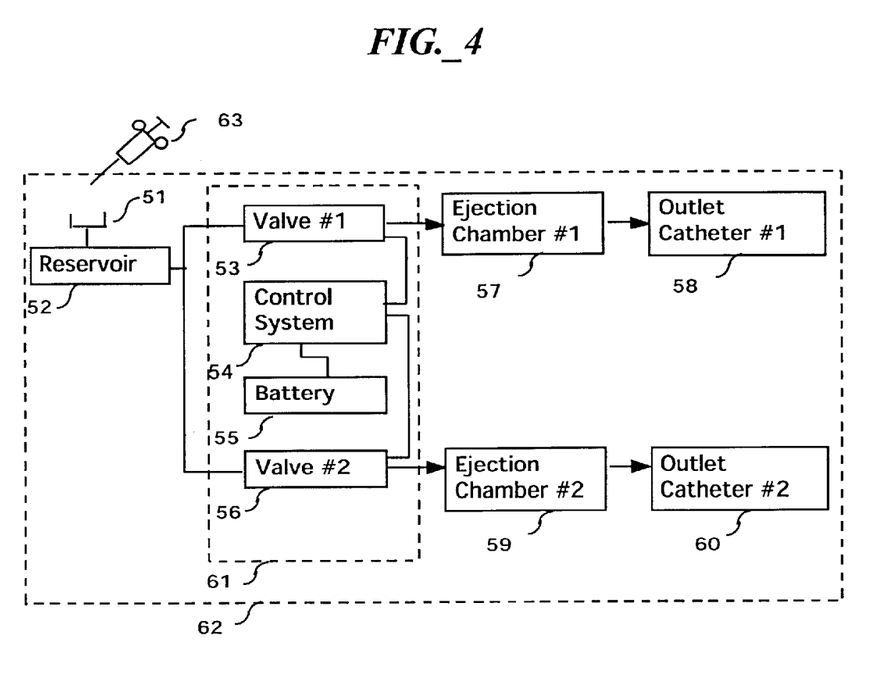
FIG. 4 shows a schematic view of a single reservoir pump with dual ejection chambers.

A pump embodiment is shown in FIG. 4 that contains a single reservoir 52 in fluid communication with two valves 53 and 56 controlled by control system 54 with power from battery 55. The reservoir has injection port 51 that can be filled with a syring 63. The valves 53 and 56, control system 54, and battery 55 form hermetically sealed module 61. The control system contains one or more sensors and appropriate circuitry to control valves 53 and 56 either as a pair or independently. Infusates to be delivered can be stored in ejection chambers 57 and 59 and directed to an appropriate body location through outlet catheters 58 and 60. As shown in FIG. 4, the entire device can be located below the cutaneous layer 62. However, one of skill in the art will recognize that the pump also can be implanted with some elements mounted percutaneously. For example, the sensor of control system 54 can be mounted percutaneously, as can injection port 51.

Figure 5:
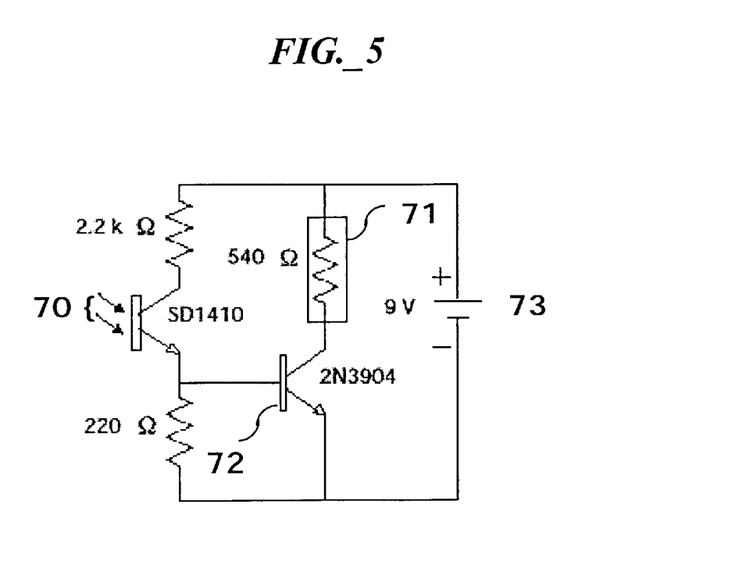
FIG. 5 shows a circuit suitable for use as a control system for a single chamber pump.

The control system comprises a circuit capable of controlling the position of the valve in response to a signal generated by the sensor. An appropriate control system for an infrared sensitive pump is shown in FIG. 5. Infrared light activates infrared sensor 70 allowing current to flow to transistor 72 and completing the circuit through valve 71 causing the valve to open. The circuit is powered by power source 73. It is within the purview of a skilled artisan to design equivalent circuits that can control the valve position in response to a signal detected by the sensor. Such a control system can be provided as discrete components or as an integrated or microelectronic circuit.

In one embodiment, the valve control system shown in FIG. 5 is built around a silicon phototransistor (Honeywell, S.Dak. 1440-004; $I_L$=6 mA @ 5 mW/cm$^2$, $\lambda$=1000 nm) that activates a transistor switch when illuminated. The circuit is powered with a miniaturized 9 V battery (Gold Peak Batteries, model 25 A; capacity: 18 mAh). The quiescent current in the controller is on the order of 200 nA, a minimum drain that would in principle allow the battery to last for >5 years with the circuit in the dark. The phototransistor current sufficient to saturate the transistor switch and energize the valve is ~0.5 mA. In such conditions, the battery current is ~27 mA which implies that a new battery will allow for ~60 min. of uninterrupted activation. Since the pump will be activated for a period of less than about 1 min. for each implantation, there is little risk that the battery will be drained empty by the controller and valve. Total active power consumption of the device is ~150 mW. In such an embodiment, the valve was activated when illuminated with a 940 nm IRLED (I=20 mA) placed 1 m away from the phototransistor in the axis of the photosensitive surface. A 100 W red light bulb placed 2 m away from the phototransistor also emitted sufficient light to activate the valve.

Figure 6:
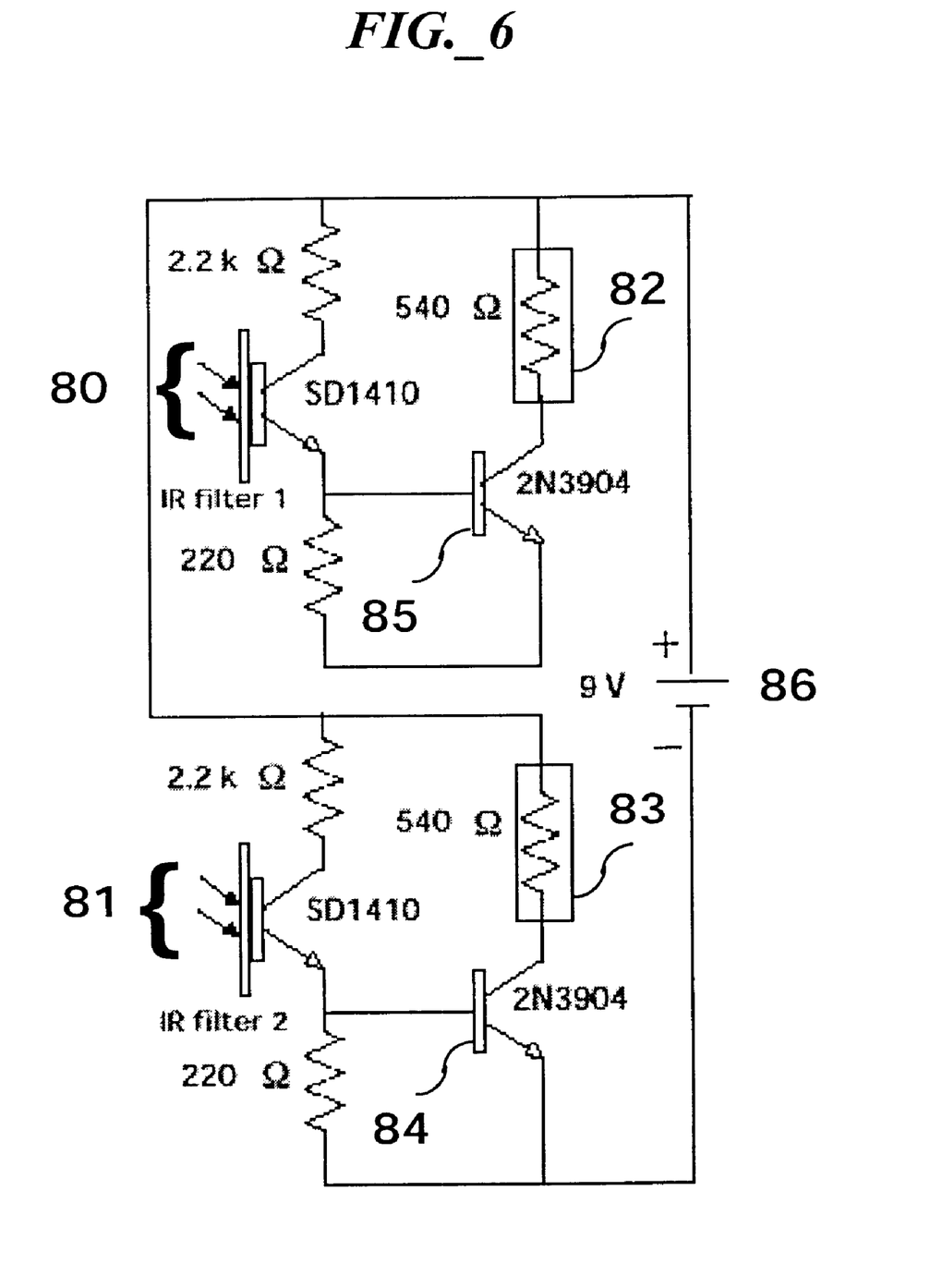
FIG. 6 shows a circuit suitable for use as a control system for a dual chamber pump.

More complex control systems also can be used with a pump of the invention. FIG. 6 shows a control system with a first infrared sensor 80 containing an infrared filter controlling first valve 82 using transistor 85 and a second infrared sensor 81 containing an infrared filter controlling second valve 83 using transistor 84. Power is supplied by power source 86. The infrared filters can be chosen such that both valves respond to the same or different wavelengths of infrared light. In other embodiments, multiple valves can be controlled by a control system that recognizes, for example, different infrared light pulse sequences.

In one embodiment, one phototransistor 80 has its transmission window covered with a color glass filter (Schott, RG 850) whose transmittance is >95% for wavelengths above 900 nm and <0.1% for wavelengths below 800 nm. Activation of this phototransistor occurs through illumination by a 100 W Quartz-Tungsten Halogen lamp (Oriel, 6359) fitted with an integral reflector and an identical glass filter (Schott, RG 850). The second phototransistor 81 is covered with a color glass filter (Schott, BG 38) with a transmittance of >30% for wavelengths below 700 nm and <5% for wavelengths above 800 rim. Activation of the second phototransistor occurs through illumination by a lamp fitted with a hot mirror filter (Ealing, model 35-6865) coupled to a long pass filter (Schott, RG 630). This will allow transmission of 600 nm to 700 nm wavelengths, while blocking the lamp's infrared output (700 nm to 1100 nm).

Sensors can be incorporated into the control system that detect any electromagnetic radiation including, for example, magnetic fields, ultraviolet, visible and infrared light. The use fo the pump can determine the appropriate choice of sensor. For example, where the pump is to be used to study animal behavior, it is advantageous to use a sensor sensitive to a signal that is not perceived by the subject animal. In one embodiment, the sensor is sensitive to a magnetic field, for example, a Reed swtich. Because magnetic fields decay extremely rapidly at increasing distance from the source, activation with a magnetic field limits allows triggering of the pump at maximum distances of approximately 12 cm when using a hand held permanent magnet. In another embodiment, the sensor detects infrared light. Because rodents perceive infrared light poorly or not at all, an infrared light activated pump can be used, for example, to study rodent behavior. In one embodiment, the sensor is an infrared sensitive phototransistor, for example, a photodarlington transistor. In such an embodiment, the infrared activated pump is triggered at distances of up to about 100 cm using a low power infrared light source. Using a higher powered light source will increase the available triggering range.

Use of infrared activated pumps also provides greater control of infusate release. The pulsatile release of the infusate can be abruptly initiated or halted with pulses of infrared light of varying duration. The use of an infrared sensor to trigger the pump allows increased specificity of the release of a drug. A pump also may contain multiple chambers or reservoirs in which individual drugs could be released sequentially or simultaneously by infrared light pulses.

The pump can be waterproofed to avoid DC leakage and corrosion at electrical joints and to avoid problems with tracking of bodily fluids along seams of the pump, as well of the possibility of condensation of moisture in spaces between the implant components. In one embodiment, all electronics (battery, valve, circuit components, sensor) are encapsulated together. The components of the pump can be encapsulated using any biocompatible material. In one embodiment, the electronic components are assembled, soldered point-to-point, and carefully cleaned of any solder flux or other surface contaminants that might interfere with the adhesion of the encapsulant. To aid assembly, the outflow and inflow ports of the valve can be provided with a temporary masking sleeve of silicone tubing. One suitable encapsulation material is a thin layer of beeswax, whose property of long-term water impermeability has historically made it a successful encapsulant for implantable electronic devices. When using beeswax, it is generally useful to stabilize the encapsulated assembly with a second more rigid biocompatible layer, for example, dimethyl silicone (Applied Silicone Corp., #40072, Los Angeles, Calif.). This medical grade silicone is suitable for long term implantation (>30 days). When assembling the pump, ports of the valve can be resleeved with protective tubing and the silicone rubber applied in such a manner that the silicone affixes itself ahead of the beeswax at the distal port. This creates a miniature silicone gasket at each port.

A sensor can be encapsulated in a material that does not interfere with operation of the sensor. An infrared sensitive sensor can, for example, be encapsulated with a material that transmits infrared light, for example, a clear, saline-resistant epoxy across the optical window of the infrared sensor.

The entire device or individual components can be sterilized with ethylene oxide gas, by irradiation, or by other suitable techniques, including sterilization by autoclave (e.g., silicone disc springs can be sterilized by steam for 20 min at 121° C.) or by a liquid sterilization solution (e.g., 3.4% glutaraldehyde).

A device can be designed according to the invention to provide a given volumetric flow rate by following Poiseuille's Law. Factors will include the pressure delivered by the reservoir, the length and inner diameter of the ejection chamber or outlet catheter, the viscosity of the infusate and the pressure at the infusion site. In an embodiment designed for implantation in a rat, for example, the large pressure head delivered by the reservoir (between 27.6 and 41.4 kPa or 4–6 PSI for those reservoirs used in the described embodiment) compared to the relatively low central venous pressure (CVP) of the rat (about 534 Pa or 4 mm Hg), means that small changes in the CVP due to positional changes of the animal should not significantly change the $\Delta P$ term, or flow rate. Flow=$(\Delta P D^4 \pi)/128 L v$ where $\Delta P$=the change in pressure between the reservoir and the central venous pressure at the site of catheter insertion; D=the inner diameter of the tubing; L=the length of the tubing; v=the viscosity of the infusate; and $\pi$ is the constant approximately equal to 3.1416.

Figure 8:
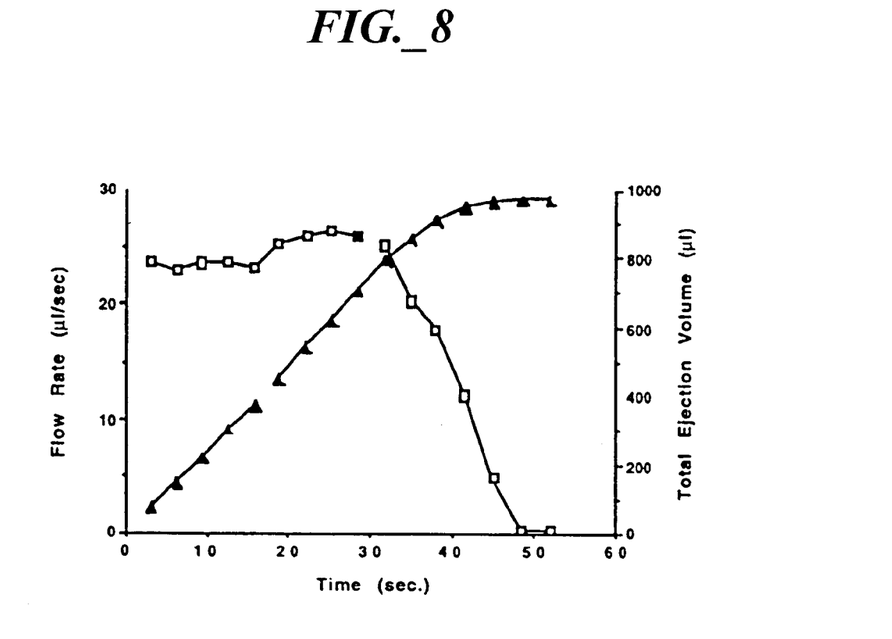
FIG. 8 demonstrates one example of the flow rate (squares) and total volume ejected (triangles) from a pump over time. The plateau flow rate (squares) of approximately 25 μl/sec was achieved using an ejection chamber constructed of 150 cm of coiled polyethylene tubing (ID 0.56 mm, PE50). Decrease in the flow noted at approximately 85% emptying reflects a decrease in the spring constant of the silastic disc reservoir as it approaches its resting position.

Flow rates of pumps also can be calibrated experimentally, for example, by measuring changes in the weight of the pump reservoir as a function of time using an accurate electronic scientific balance equipped with a data acquisition or printing interface. A pressurized receptacle can be used to approximate the pressure at the infusion site (e.g., 534 Pa for the rat central venous system). Pumps also can be calibrated with the outlet catheter located at the desired infusion site of a live, anesthetized animal. Calibration allows accurate delivery of discrete boluses to an animal by controlling the length of time a valve is held in the open position using the remote activated control system. In various embodiment, the entire ejection chamber can be delivered in a period of less than about an hour, preferably in a period of less than about 15 minutes, more preferably in a period of about 1 minute or less. For example, in one embodiment shown in FIG. 8, a pump capable of delivering about 1000 ul was able to deliver the entire volume in a period of about 5 seconds.

EXAMPLES

Example 1

Infrared Activated Pump Suitable for Implantation in Rats

A pump of the invention was constructed at an appropriate size for use with rats from a 25 mm diameter×6.6 mm high, silicone disc spring (Esox Technology, Corp., Eagan, Minn.) with a reservoir volume of 1.1 ml and a 0.1 ml dead volume (infusate remaining in the pump when the elastomer spring has nested). The reservoir provided an outlet pressure of about 4 to about 6 PSI ( about 27.6 to about 41.4 kPa). The reservoir backing was formed from 316 stainless steel with a poly-carbonate needle stop, covered in medical grade silicone.

The control system was equipped with a photosensor (Honeywell Inc.) with surrounding 10 mm×3 mm percutaneous skin button (Kent Scientific Corp., Litchfield, Conn.).

The sensor could be activated by infrared light ($I_L$=6 mA @ 5 mW/cm$^2$; λ=1000 nm; $I_{CEO}$=100 nA). The control system also included a 9 Volt DC alkaline battery (model GP25A-C1, Gold Peak Industries) with solderable poles at opposing ends. The battery had a capacity of 18 mAh and dimensions of 8.0 mm×21.9 mm.

The pump also included an electrically activated solenoid valve (The Lee Company, Essex, Conn.) capable of operating with an inlet pressure of 0–25 psia (0–172 kPa) and having a pressure differential of 10 psid (69 kPa). The valve required 250 mW to hold open and had a resistance of 576 ohms, a cycle life of 100,000,000 cycles (Liquid) and a flow resistance of 2500 Lohms, an operating temperature range of 4° C.–49° C. and a response time of 2.5 ms. The valve had dimensions of about 5.33 mm×21.34 mm with a Ni—Fe Alloy armature and a LCP Vectra-Celanese liquid crystal polymer housing. The entire valve assembly was embedded in medical grade silicone (Applied Silicone, Corp., Los Angeles, Calif.).

The pump also had a coiled ejection chamber which was fabricated from coiled polyethylene tubing (Intramedic, Clay Adams, Parsippany, N.J.) of variable length and diameter. In this example, the outflow catheter tip (silastic, 12 cm, c.a. 32 microliter, I.D. 0.58 mm) was telescoped into the outflow port of the ejection chamber. The ejection chamber was fabricated from a piece of polyethylene tubing (41.3 cm, ca. 240 microliters, I.D. 0.86 mm) and silicone. The polyethylene tubing was coiled either into a cylinder or else as a series of loops layered into a flattened disc and afixed using silicone. Typical ranges for dimensions of tubing for applications in rats and mice are I.D. 0.1 to 1.5 mm and lengths of 25 to 150 cm.

The pump also included an outflow catheter of medical grade RENASIL™ (Braintree Scientific, Braintree, Mass.) medical grade silastic with an inner diameter (ID) of 0.58 mm and an outer diameter (OD) of 0.97 mm. Prior to implantation the outflow catheter was filled with a heparin solution (NaCl 9%+heparin 1000 U/ml).

Example 2
Magnetically Activated Pump Suitable for Implantation in Rats

A magnetically activated pump of the invention was constructed at an appropriate size for use with rats. The pump was assembled prior to implantation. A silicone disc spring (Kent Scientific, 25 mm diameter, 7 mm height) acts as the reservoir and contains normal saline. Connection is made to an electrically activated microvalve (as in Example 1) whose resting state is in the closed position. A magnetically activated (H) Reed switch allows current from the battery to open the valve when activated by a hand-held Nb—Fe—B magnet. This results in release of the contents of the reservoir, thereby permitting bolus injection of the contents of the tubing connected to the outflow port of the valve. Because of the acute sensitivity of the Reed switch, flow from the pump can be intermittent provided the magnetic field is applied intermittently. This permits the sequential release of any number of drugs loaded into the tubing. The outflow rate is controlled by the length and diameter of the tubing. The rate also can be controlled with a flow restrictor. A flow restrictor can be a porous membrane or can be a non-porous membrane with one or more apertures.

The pump was implanted subcutaneously on the dorsum of a rat. The tip of the silastic catheter was tunneled subcutaneously and placed into the external jugular vein. The pump may be triggered and animals tested hours to days following recovery from this relatively minor surgical procedure.

All references cited in the instant specification are hereby incorporated by reference in their entirety.

What is claimed is:

1. An implantable pump for delivery of a drug, the implantable pump comprising:
   a reservoir that deforms elastically when it is filled with the drug;
   an outlet catheter in fluid communication with said reservoir;
   a valve in fluid communication with said outlet catheter, wherein said valve is electrically activated; and
   a control system comprising a sensor, wherein said sensor generates a control signal for controlling said valve when electromagnetic radiation interacts with said sensor.

2. The pump of claim 1 wherein said sensor is activated magnetically.

3. The pump of claim 1 wherein said sensor is light-activated.

4. The pump of claim 3 wherein said sensor is infrared light-activated.

5. The pump of claim 4 wherein said sensor is a phototransistor.

6. The pump of claim 1 wherein said reservoir is silicone.

7. The pump of claim 1 wherein said valve is a solenoid valve.

8. The pump of claim 1 further comprising an inlet port in fluid communication with said reservoir, said inlet port having a resealable septum.

9. The pump of claim 8 wherein said inlet port further comprises a filter disposed between said septum and said reservoir.

10. The pump of claim 1 wherein said reservoir can contain volume of between about 100 microliters and 5000 microliters.

11. The pump of claim 1 wherein said outlet catheter is polyethylene, polytetrafluoroethylene, polyurethane or silastic tubing.

12. The pump of claim 1 further comprising an ejection chamber in fluid communication with said outlet catheter.

13. The pump of claim 12 wherein said ejection chamber is polyethylene, polytetrafluorethylene, polyurethane or silastic tubing.

14. The pump of claim 1 further comprising a flow restricting device in fluid communication with said reservoir.

15. The pump of claim 14 wherein said flow restricting device is a porous membrane.

16. The pump of claim 14 wherein said flow restricting device is non-porous and has one or more apertures.

17. The pump of claim 1 wherein said reservoir has a substantially rigid backing member.

18. The pump of claim 1 wherein said elastically deformable member is a Belleville washer.

19. An implantable pump for drug delivery comprising: a reservoir having an elastically deformable member and a substantially rigid backing member; a solenoid valve in fluid communication with said outlet catheter, wherein said valve has a closed resting position; an outlet catheter in fluid communication with said valve; and a control system having an infrared sensor and an electronic circuit controlling said valve.

20. An implantable pump for delivery of a drug, the implantable pump comprising:
   a reservoir that deforms elastically when it is filled with the drug;

an outlet catheter in fluid communication with said reservoir;

a valve in fluid communication with said outlet catheter, wherein said valve is electrically activated;

a source of infrared radiation;

a control system comprising a sensor for detecting infrared radiation from said source, wherein said sensor generates a control signal for controlling said valve when said sensor detects infrared radiation.

21. The implantable pump of claim 20, wherein the sensor comprises a silicon phototransistor.

22. The implantable pump of claim 20, wherein said drug flows through said implantable pump at a flow rate of about 1 microliters per hour to about 50 microliters per hour.

23. The implantable pump of claim 20, wherein said drug flows through said implantable pump at a flow rate of about 10 microliters per second to about 500 microliters per second.

24. The implantable pump of claim 20, wherein said drug flows through said implantable pump at a flow rate of about 200 microliters per second.

25. The implantable pump of claim 20 further comprising:

a second reservoir that deforms elastically when it is filled with a second drug;

a second valve in fluid communication with said outlet catheter, wherein said valve is electrically activated;

a second source of infrared radiation; and a control system comprising a second sensor for detecting infrared radiation from said second source, wherein said second sensor generates a control signal for controlling said second valve when said second sensor detects infrared radiation.

* * * * *